United States Patent
Jasper et al.

(10) Patent No.: US 9,752,076 B2
(45) Date of Patent: *Sep. 5, 2017

(54) COMPOUNDS FOR A LIQUID-CRYSTALLINE MEDIUM, AND THE USE THEREOF FOR HIGH-FREQUENCY COMPONENTS

(75) Inventors: Christian Jasper, Darmstadt (DE); Elvira Montenegro, Weinheim (DE); Detlef Pauluth, Ober-Ramstadt (DE); Volker Reiffenrath, Rossdorf (DE); Atsutaka Manabe, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 908 days.

This patent is subject to a terminal disclaimer.

(21) Appl. No.: 13/505,761

(22) PCT Filed: Oct. 6, 2010

(86) PCT No.: PCT/EP2010/006091
§ 371 (c)(1), (2), (4) Date: Jul. 9, 2012

(87) PCT Pub. No.: WO2011/054425
PCT Pub. Date: May 12, 2011

(65) Prior Publication Data
US 2012/0267571 A1   Oct. 25, 2012

(30) Foreign Application Priority Data
Nov. 4, 2009 (DE) .................. 10 2009 051 906

(51) Int. Cl.
| | |
|---|---|
| C09K 19/32 | (2006.01) |
| C09K 19/42 | (2006.01) |
| C07C 13/47 | (2006.01) |
| C07C 13/573 | (2006.01) |
| C07C 15/24 | (2006.01) |
| C07C 15/28 | (2006.01) |
| C07C 21/185 | (2006.01) |
| C07C 21/19 | (2006.01) |
| C07C 21/22 | (2006.01) |
| C07C 22/08 | (2006.01) |

(52) U.S. Cl.
CPC .............. *C09K 19/32* (2013.01); *C07C 13/47* (2013.01); *C07C 13/573* (2013.01); *C07C 15/24* (2013.01); *C07C 15/28* (2013.01); *C07C 21/185* (2013.01); *C07C 21/19* (2013.01); *C07C 21/22* (2013.01); *C07C 22/08* (2013.01); *C09K 19/322* (2013.01); *C09K 19/42* (2013.01); *C09K 2219/11* (2013.01)

(58) Field of Classification Search
CPC ...... C09K 19/16; C09K 19/32; C09K 19/322; C09K 2019/0459; C09K 2019/328; C07C 13/48; C07C 13/58; C07C 2102/88; C07C 21/185; C07C 21/19; C07C 21/22; C07C 22/08; C07C 13/47; C07C 13/573; C07C 15/24; C07C 15/28
See application file for complete search history.

(56) References Cited

U.S. PATENT DOCUMENTS

| | | | | |
|---|---|---|---|---|
| 3,991,049 A | * | 11/1976 | Siegrist et al. | 546/350 |
| 4,786,709 A | * | 11/1988 | Iimura et al. | 528/298 |
| 5,082,587 A | * | 1/1992 | Janulis | 252/299.01 |
| 5,482,650 A | * | 1/1996 | Janulis et al. | 252/299.01 |
| 5,851,427 A | | 12/1998 | Kelly | |
| 6,549,188 B1 | * | 4/2003 | Takeichi et al. | 345/97 |
| 7,361,288 B2 | | 4/2008 | Lüssem et al. | |
| 7,768,404 B2 | | 8/2010 | Flores et al. | |
| 8,197,709 B2 | * | 6/2012 | Lietzau | C09K 19/20 252/299.61 |
| 8,747,695 B2 | * | 6/2014 | Jasper | C07C 15/58 252/299.61 |
| 8,999,198 B2 | * | 4/2015 | Reiffenrath | C09K 19/18 252/299.63 |
| 9,169,438 B2 | * | 10/2015 | Reiffenrath | C07C 25/24 |
| 9,175,219 B2 | * | 11/2015 | Jasper | C09K 19/3001 |
| 2005/0067605 A1 | | 3/2005 | Lussem et al. | |
| 2008/0309864 A1 | | 12/2008 | Lee et al. | |
| 2009/0278744 A1 | * | 11/2009 | Kirino et al. | 343/700 MS |
| 2010/0012929 A1 | | 1/2010 | Nakano et al. | |

FOREIGN PATENT DOCUMENTS

| | | |
|---|---|---|
| CN | 101279888 A | 10/2008 |
| DE | 10 2004 029429 | 2/2005 |

(Continued)

OTHER PUBLICATIONS

English Translation of KR2004060265.*

(Continued)

*Primary Examiner* — Cynthia H Kelly
*Assistant Examiner* — Anna Malloy
(74) *Attorney, Agent, or Firm* — Millen White Zelano & Branigan, PC

(57) ABSTRACT

The present invention relates to compounds of the formula I

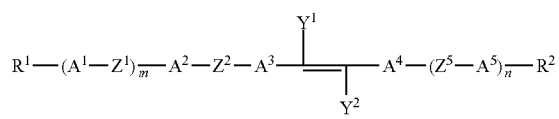

where one or more of the radicals $A^{1-5}$ denote a 1,4-naphthylene or 1,4- or 9,10-anthracenylene radical, and the other parameters are as defined in Claim 1. The invention additionally includes liquid-crystalline media which comprise the title compounds, and components for high-frequency technology which comprise these media, in particular phase shifters and microwave array antennae.

15 Claims, No Drawings

(56) References Cited

FOREIGN PATENT DOCUMENTS

| | | |
|---|---|---|
| EP | 0 731 084 | 9/1996 |
| EP | 2 073 290 | 3/2009 |
| GB | 2 210 381 | 6/1989 |
| JP | 5198261 A | 8/1976 |
| JP | 02117915 A | 5/1990 |
| JP | 03163186 A | 7/1991 |
| JP | 04164037 A | 6/1992 |
| JP | 05178810 A | 7/1993 |
| JP | 05179240 A | 7/1993 |
| JP | 05239454 A | 9/1993 |
| JP | 2002212114 A * | 7/2002 |
| JP | 2004 82439 | 3/2004 |
| JP | 2005 120208 | 5/2005 |
| JP | 2006182730 A | 7/2006 |
| JP | 2010522207 A | 7/2010 |
| JP | 2013515750 A | 5/2013 |
| KR | 2004060265 A * | 7/2004 |
| WO | WO-2008 002120 | 1/2008 |

OTHER PUBLICATIONS

English Translation of JP2002212114.*
Hahn et al., "A Study of the Relationship between the Color and Structure of Organic Compounds II Synthesis and Properties of 1,4-divinylnaphthalene Derivatives", 1970, Roczniki Chemii, 44, 115-119.*
Chang, C. et al., "Synthesis of laterally substituted α-methylstilbene-tolane liquid crystals," Liquid Crystals, Jan. 2008, vol. 35, No. 1, pp. 1-9.
Dainippon Ink & Chem Inc., "Varible function device," Patent Abstract of Japan, Publication Date: May 12, 2005; English Abstract of JP-2005 120208.
Gaebler, A. et al., "Liquid crystal-reconfigurable Antenna Concepts for Space Applications at Microwave and Millimeter waves," International Journal of Antennas and Propagation, 2009, 7 pages.
International Search Report for PCT/EP2010/006091 dated Jan. 19, 2011.
Mitsui Chemicals Inc., "Optical recording medium and diaryl acetylenic compound," Patent Abstracts of Japan, Publication Date: Mar. 18, 2004; English Abstract of JP-2004 082439.
Mohammady, S. Z. et al., "Effect of steric factors on mesomorphic stability I. 4-(4-Substituted phenylazo)-1-naphthyl 4-alkoxybenzoates," Liquid Crystals, Apr. 2005, vol. 32, No. 4, pp. 477-482.
Chinese Office Action for 201080048996.3 (Jul. 10, 2013).
S. Akiyama et al., "Direct CC Triple Bond Formation from the CC Double Bond with Potassium tert-Butoxide in Dimethylformamide Containing Trace Amounts of Oxygen", Journal of the Chemical Society, Chemical Communications (1991) pp. 948-950.
Japanese Office Action dated Nov. 26, 2014 corresponding to Japanese Application No. 2012-537308.
Luo et al., "Conjugated Oligothiophene-anthracene Co-oligomers: Synthesis", Physical Properties, and Self-assembly; Journal of Materials Chemistry, 2009, 19(43), pp. 8202-8211.
Xin et al., "Synthesis of 9, 10-Bis (4-alkoyxystyryl) anthracene Derivatives and Their Fluorescent Properties", Hecheng Huaxue, 2009, 17(2), pp. 164-166.
Kim et al., "Intraparticle Energy Transfer and Fluorescene Photoconversion in Nanoparticles", An Optical Highlighter Nanoprobe for Two-Photon Bioimaging, Chemistry of Materials, 2007, 19(23), pp. 5650-5656.
Chochos et al., "Synthesis, Optical and Morphological Characterization of Soluble Main Chain 1,3,4-oxadiazole Copolarylethers-potential Candicates for Solar Cells Applications as Electron Acceptors", Polyer, 2005, 46(13), pp. 4654-4663.
Konstandakopoyloy et al. "Soluble Rigid-Flexible Polyethers Containing Bis(biphenyl) anthracene or Bis(styryl) anthracene Units in the Main Chain for Light-Emitting Applications", Journal of Polymer Science, Part A: Polymer Chemistry, 1999, 37(2), pp. 3826-3837.
Kim et al., "Electroluminescent Properties of Anthracene-Based Dyes with Methoxy-Naphthylethenyl Substituent", Korea Polymer Journal, 1999, 7(1), pp. 18-23.
Novikova et al., "Aromatic Copolyamides and Copolyesters with Vinylenarylene and Terthiophene Fragments in the Polymer Chain", Synthesis and Photophysical Properties, Synthetic Metals, 1996, 83(1), pp. 47-55.
Weitzel et al., "Polyarylenes and poly(arlenevinylene)s, 3a)", Oligomeric Model Compounds for poly(9,10-anthrylenevinylene), Makromolekulare Chemie, 1990, 191(11), pp. 2815-2835.
Horhold et al., Faserforschung und Textiltechnik, 1978, 29(6), pp. 393-395.
Saikachi et al., "Reaction of Aromatic p-Substituted Bisphosphoranes with Bisaldehydes", Chemical & Pharmaceutical Bulletin, 1971, 19(5), pp. 959-969.
Hahn et al., Roczniki Chemii, 1970, 44(1), pp. 115-119.
Tzanetos et al., "Side-Chain Terpyridine Polymers through Atom Transfer Radical Polymerization and Their Ruthenium Complexes", Journal of Polymer Science, Part A: Polymer Chemistry, 2005, 43(20), pp. 4838-4848.
Konishi et al., "Large Domain Film of Bis(styrilanthracene) Derivatives Prepared by a Simple Melt-Freezing Process and the Improvement of Field Effect Hole Mobility", Japanese Journal of Applied Physics, 2008, 47(6, Pt. 1), pp. 4732-4735.
Li et al., "Styryl-Based Compounds as Potential in vivo Imaging Agents for B-Amyloid Plaques", ChemBioChem, 2007, 8(14), pp. 1679-1687.
Naito et al., "Photoluminescence Properties of Nonpolymeric Amorphous Dyes", Japanese Journal of Applies Physics, part 1: Regualr Papers, Short Notes & Review Papers, 1999, 38(5A), pp. 2792-2798.
Akiyama et al., "Direct C-C Triple Bond Formation from the C-C Double Bond with Potassium tert-Butoxide in Dimethylformamide Containing Trace Amounts of Oxygen", Journal of the Chemical Society, Chemical Communications, 1991, (14), pp. 948-950.
Siegrist et al., Helvetica Chimica Acta, 1969, 52(8), pp. 2521-2554.
English Abstract for Chinese Application No. 101279888, published Oct. 8, 2008.
English Abstract for Japanese Application No. 2006182730; published Jul. 13, 2006.
English Abstract for Japanese Application No. 05178810; published Jul. 20, 1993.
English Abstract for Japanese Application No. 03163186; published Jul. 15, 1991.
English Abstract for Japanese Application No. 02117915; published May 2, 1990.
English Abstract for Japanese Application No. 05179240; published Jul. 20, 1993.
English Abstract for Japanese Application No. 05239454; published Sep. 17, 1993.
English Abstract for Japanese Application No. 04164037; published Jun. 9, 1992.
English Abstract for Japanese Application No. 5198261; published Aug. 30, 1976.
English Abstract for Japanese Application No. 2010522207; published Jul. 1, 2010.
English Abstract for Japanese Application No. 2013515750; published May 9, 2013.

* cited by examiner

COMPOUNDS FOR A LIQUID-CRYSTALLINE MEDIUM, AND THE USE THEREOF FOR HIGH-FREQUENCY COMPONENTS

The present invention relates to aromatic compounds containing at least one double bond and at least one 1,4-naphthylene radical or 1,4- or 9,10-anthracenylene radical, to the use thereof for high-frequency components, to liquid-crystalline media comprising the compounds, and to high-frequency components comprising these media, in particular antennae, especially for the gigahertz range. The liquid-crystalline media serve, for example, for the phase shifting of microwaves for tuneable "phased-array" antennae.

Liquid-crystalline media have been used for some time in electro-optical displays (liquid crystal displays—LCDs) in order to display information.

Recently, however, liquid-crystalline media have also been proposed for use in components for microwave technology, such as, for example, in DE 10 2004 029 429 A and in JP 2005-120208 (A).

An industrially valuable application of liquid-crystalline media in high-frequency technology is based on their property that their dielectric properties can be controlled, particularly for the gigahertz range, by a variable voltage. This enables the construction of tuneable antennae which do not contain any moving parts (A. Gaebler, A. Moessinger, F. Goelden, et al., "Liquid Crystal-Reconfigurable Antenna Concepts for Space Applications at Microwave and Millimeter Waves", International Journal of Antennas and Propagation, Vol. 2009, article ID 876989, 7 pages, 2009, doi: 10.1155/2009/876989).

A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, 545-548, describe, inter alia, the properties of the known single liquid-crystalline substance K15 (Merck KGaA, Germany) at a frequency of 9 GHz.

A compound of the formula

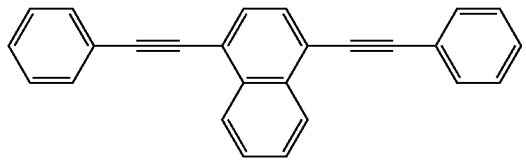 [SMILES: C(#Cc1ccc(C#Cc2ccccc2)c2ccccc12)c1ccccc1]

or derivatives thereof are described as constituents of organic thin-film transistors (EP 2 073 290 A1), as photo-sensitising dyes for the control of photoacid generating systems (WO 2008/021208 A2) and as constituents of data recording media (JP 2004-082439 A). Liquid-crystalline properties and the use thereof in liquid-crystalline media have not been described to date.

DE 10 2004 029 429 A describes the use of conventional liquid-crystal media in microwave technology, inter alia in phase shifters. This document has already investigated liquid-crystalline media with respect to their properties in the corresponding frequency range.

However, the compositions or individual compounds known to date are generally afflicted with disadvantages. Most of them result, besides other deficiencies, in disadvantageously high losses and/or inadequate phase shifts or inadequate material quality.

For use in high-frequency technology, liquid-crystalline media having particular, hitherto rather unusual, uncommon properties, or combinations of properties, are required.

Novel components for liquid-crystalline media having improved properties are thus necessary. In particular, the loss in the microwave range must be reduced and the material quality ($\eta$) improved.

In addition, there is a demand for an improvement in the low-temperature behaviour of the components. An improvement in both the operating properties and the shelf life is necessary here.

Thus, there is a considerable demand for liquid-crystalline media having suitable properties for corresponding practical applications.

Surprisingly, it has now been found that it is possible, using the compounds according to the invention, to achieve liquid-crystalline media having a suitable nematic phase range and high $\Delta n$ which do not have the disadvantages of the prior-art materials, or at least only do so to a considerably reduced extent.

The invention relates to compounds of the formula I

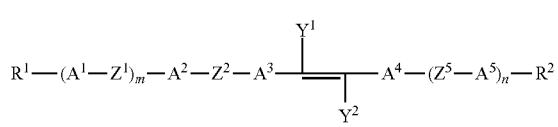

in which $A^{1-5}$, independently of one another, denote a) a radical of the formula

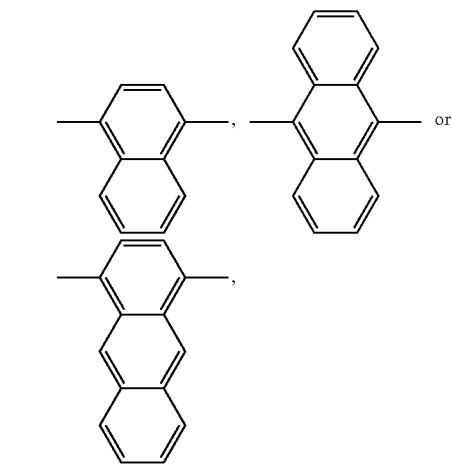

b) 1,4-phenylene, in which one or more, preferably one or two, CH groups may be replaced by N, c) trans-1,4-cyclohexylene or cyclohexenylene, in which, in addition, one or two non-adjacent CH$_2$ groups may be replaced by —O— and/or —S— and in which H may be replaced by F, or d) a radical from the group 1,4-bicyclo[2.2.2]octylene, cyclobut-1,3-diyl, spiro[3.3]heptane-2,6-diyl, thiophene-2,5-diyl, thiophene-2,4-diyl, furan-2,5-diyl, furan-2,4-diyl,

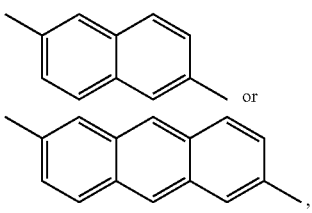

or and in which, in groups a), b), c) and d),
one or more H atoms may also be replaced by Br, Cl, F, CN, —NCS, —SCN, $SF_5$, $C_1$-$C_{10}$ alkyl, $C_1$-$C_{10}$ alkoxy or a mono- or polyfluorinated $C_1$-$C_{10}$ alkyl or alkoxy group,
and where
at least one radical from $A^1$ to $A^5$, preferably from $A^2$, $A^3$ and $A^4$, represents a radical according to a),
$R^1$ and $R^2$ each, independently of one another, denote a halogenated or unsubstituted alkyl radical having 1 to 15 C atoms, where, in addition, one or more $CH_2$ groups in these radicals may each be replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another, F, Cl, Br, CN, $CF_3$, $OCF_3$, SCN, NCS or $SF_5$,
$Z^2$ denotes —C≡C— or

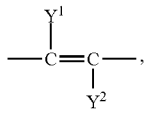

$Y^1$, $Y^2$, independently of one another, denote H, F, Cl, $C_1$-$C_{10}$ alkyl, preferably H or F, particularly preferably F,
$Z^1$, $Z^5$, independently of one another, denote a single bond, —C≡C—, —CH=CH—, —$CH_2$O—, —(CO)O—, —$CF_2$O—, —$CF_2CF_2$—, —$CH_2CF_2$—, —$CH_2CH_2$—, —$(CH_2)_4$—, —CH=CF— or —CF=CF—, where asymmetrical bridges may be oriented to both sides, and
m, n, independently of one another, denote 0, 1 or 2.

The double bonds between the rings $A^2$ to $A^4$ preferably have the transconfiguration.

The compounds according to the invention have a low melting point, a high clearing point, an extremely high optical anisotropy (Δn) and an advantageously high rotational viscosity. Alone or in a mixture with further mesogenic components, they have a nematic phase over a broad temperature range. These properties make them particularly suitable for use in components for high-frequency technology, in particular in liquid-crystalline phase shifters. Liquid-crystalline media according to the invention have the corresponding properties, for example a broad phase range and in addition good low-temperature stability.

Preferably, one or two of the radical from $A^2$, $A^3$ and $A^4$ represent(s) an optionally substituted 1,4-naphthylene radical in accordance with definition a) of the radicals. Particularly preferably, at least radical $A^3$ is a 1,4-naphthylene radical in accordance with definition a). Of the radicals from the group a), the 1,4-naphthylene radical is particularly preferred.

The index m is preferably 0 or 1, particularly preferably 0. The index n is preferably 0 or 1, particularly preferably 0.

The ring groups $A^1$ and $A^5$ are, independently of one another, preferably a 1,4-phenylene, in which, in addition, one or more H atoms may be replaced by Br, Cl, F, CN, alkyl ($C_1$-$C_{10}$), methoxy or a mono- or polyfluorinated methyl or methoxy group.

The bridge groups $Z^1$ and $Z^5$ are, independently of one another, preferably a single bond, —C≡C—, —CF=CF— or —CH=CH—, particularly preferably a single bond.

$Z^2$ is preferably —C≡C— or —CF=CF—, particularly preferably —C≡C—.

$Y^1/Y^2$ are preferably H/H, H/F, F/H, F/F, $CH_3$/H or H/$CH_3$ and particularly preferably F/F.

One of the radicals $R^1$ or $R^2$, preferably $R^1$, preferably denotes a straight-chain alkyl radical having 1 to 15 C atoms, where, in addition, one or more $CH_2$ groups in these radicals may each be replaced, independently of one another, by —C≡C—, —CH=CH—, —(CO)O—, —O(CO)—, —(CO)—, —O— or —S— in such a way that O or S atoms are not linked directly to one another.

Of the radicals from group a) for $A^{1-5}$ or preferably $A^{2-4}$, the radicals with 1,4-substitution are preferred, particularly preferably the 1,4-naphthylene radical.

Preferred embodiments of the invention are therefore selected from the following illustrative structures:

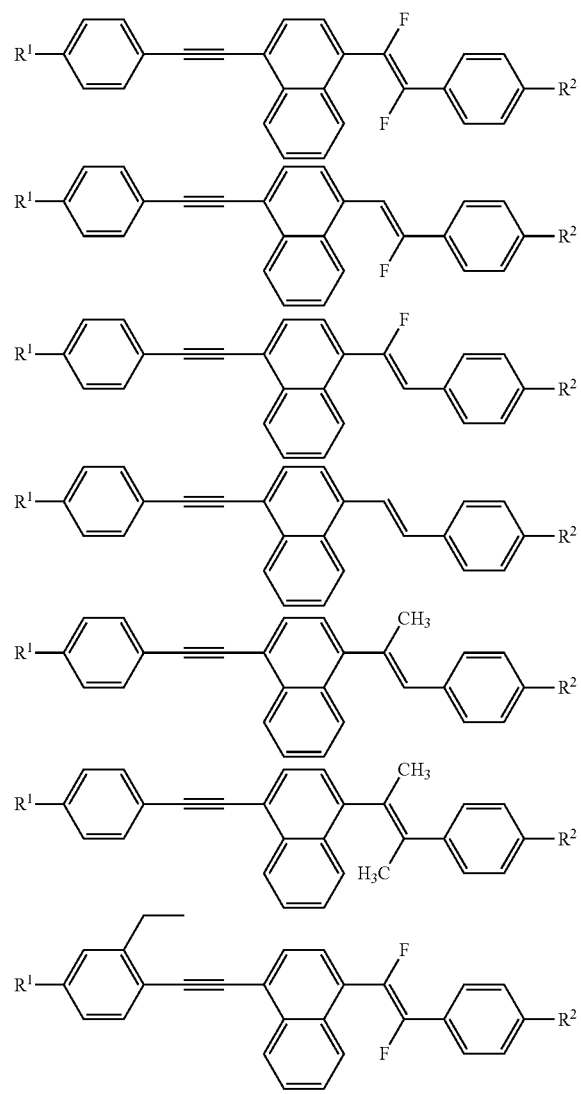

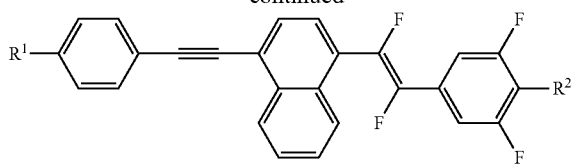
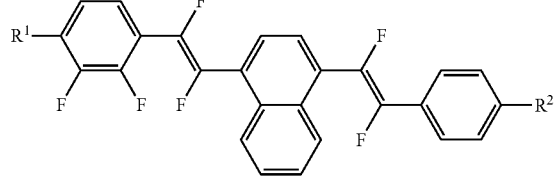
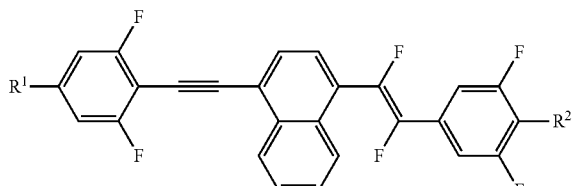
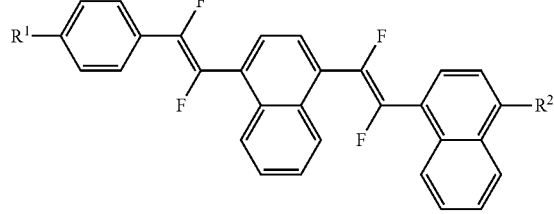
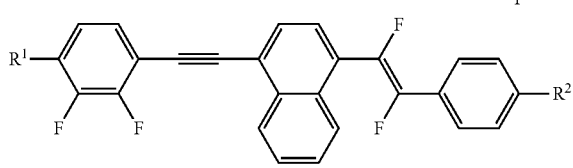
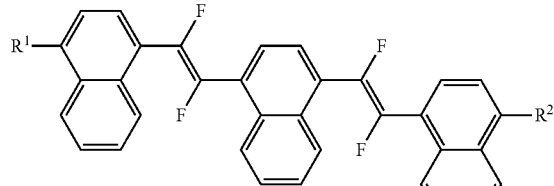
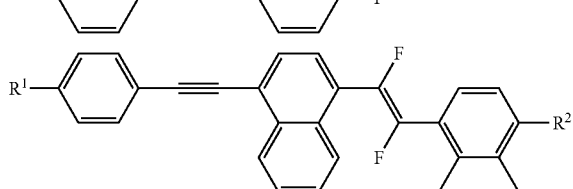
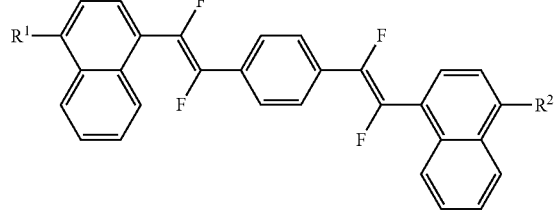
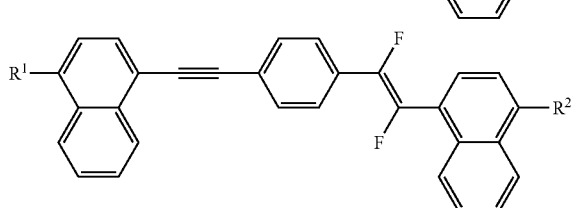
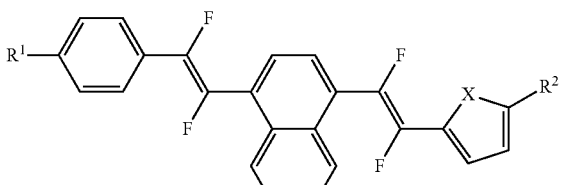
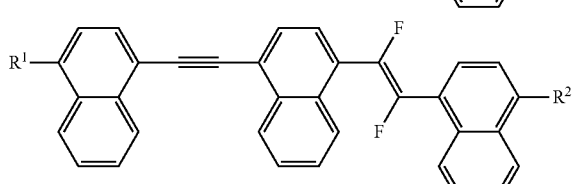
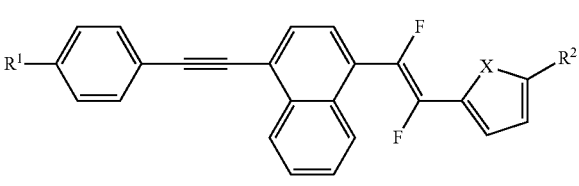
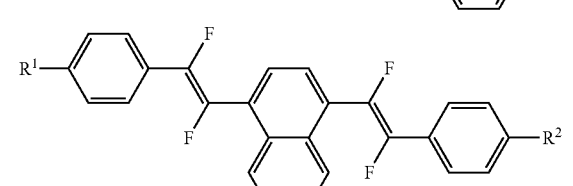
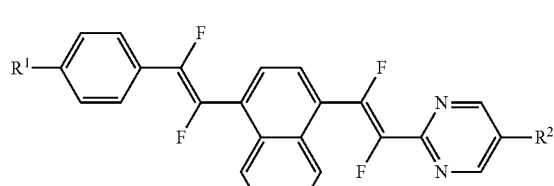
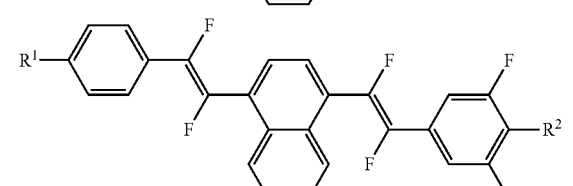

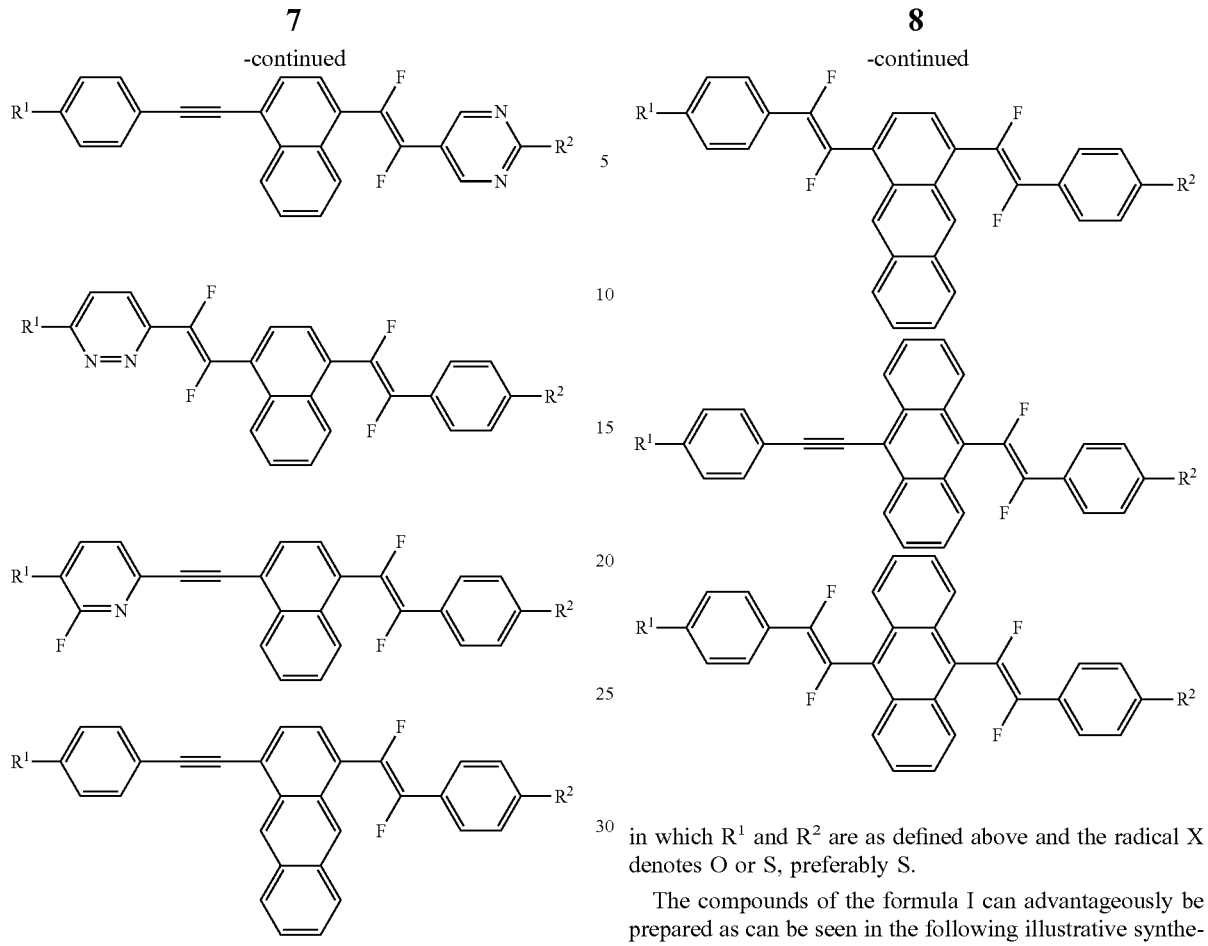
in which $R^1$ and $R^2$ are as defined above and the radical X denotes O or S, preferably S.
The compounds of the formula I can advantageously be prepared as can be seen in the following illustrative synthesis (Scheme 1):
Scheme 1. Illustrative synthesis of the compounds of the formula I; R is defined in accordance with $R^{1/2}$.
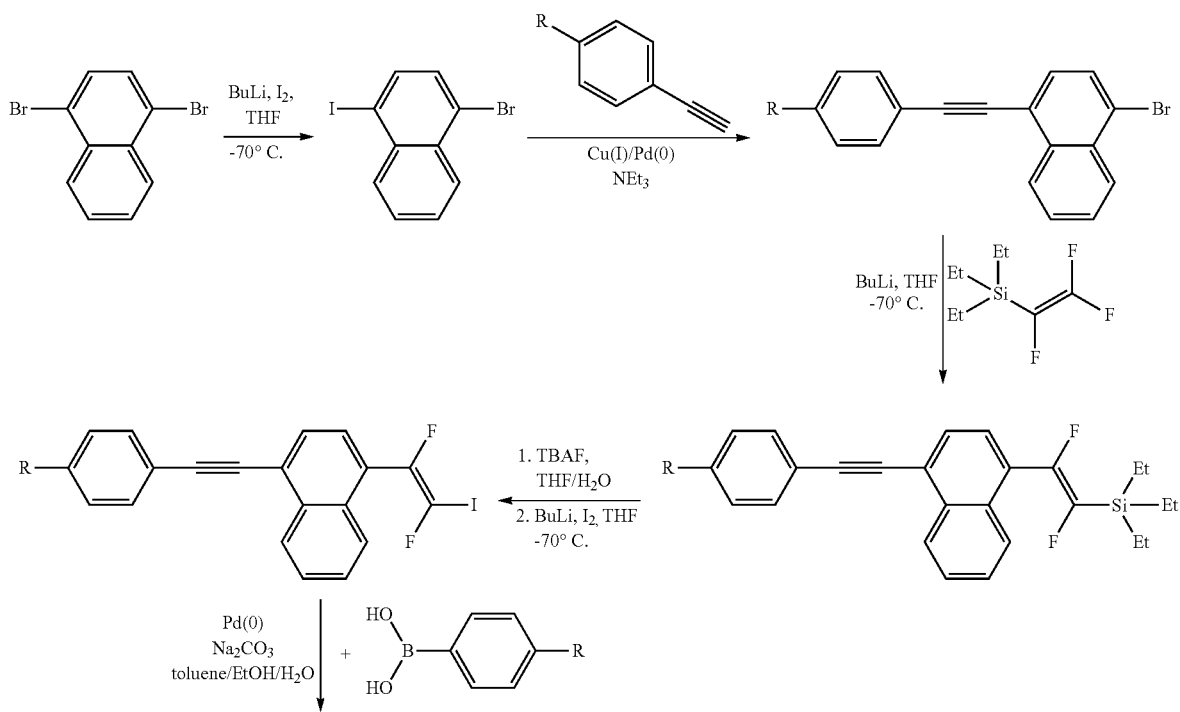

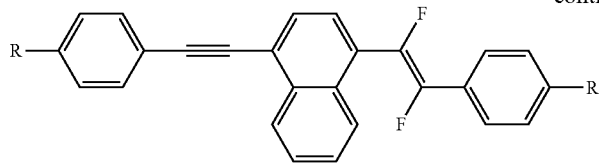

1,4-Dibromonaphthalene is subjected to a halogen-metal exchange reaction and converted into 1-iodo-4-bromonaphthalene. This is firstly converted selectively into the monofunctionalised acetylene-bridged compound in a Sonogashira coupling, followed by an addition reaction at the 1,1,2-trifluorotriethylsilylethene building block, which is known from the literature (building-block synthesis taken from: F. Babudri, A. Cardone et al., *Eur. J. Org. Chem.* 2008, 1977-1982).

After deprotection and conversion into the corresponding difluoroethylene iodide, a final Suzuki reaction with an arylboronic acid results in the desired target compounds of the formula I, in this example with an acetylene and a 1,2-difluoroethylene bridge.

The anthracene derivatives are prepared from corresponding starting compounds, such as the naphthalene derivatives.

The liquid-crystalline media in accordance with the present invention comprise one or more compounds of the formula I and optionally at least one further, preferably mesogenic compound. The liquid-crystal medium therefore preferably comprises two or more compounds, which are preferably liquid-crystalline. Preferred media comprise the preferred compounds of the formula I.

Further components of the liquid-crystalline media are preferably selected from the compounds of the formula II:

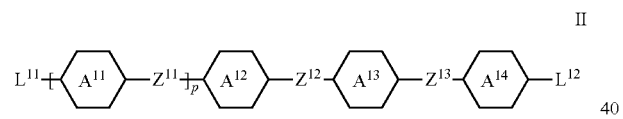

II in which
$L^{11}$ denotes $R^{11}$ or $X^{11}$,
$L^{12}$ denotes $R^{12}$ or $X^{12}$,
$R^{11}$ and $R^{12}$, independently of one another, denote unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl,
$X^{11}$ and $X^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl,
p denotes 0 or 1,
$Z^{11}$ to $Z^{13}$, independently of one another, denote trans-CH═CH—, trans-CF═CF—, —C≡C— or a single bond, and

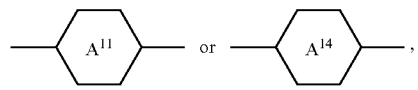

Independently of one another, denote
a) 1,4-phenylene, in which one or more, preferably one or two, CH groups may be replaced by N,
b) trans-1,4-cyclohexylene or cyclohexenylene, in which, in addition, one or two non-adjacent CH$_2$ groups may be replaced by —O— and/or —S— and in which H may be replaced by F,
and in which, in groups a) and b),
one or more H atoms may also be replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group,
preferably denote, independently of one another,

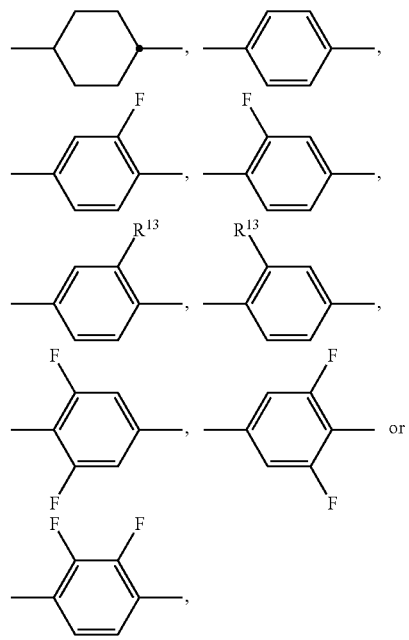

where $R^{13}$ denotes Cl, C$_{1-7}$-alkyl or C$_{3-6}$-cycloalkyl.

In a preferred embodiment of the present invention, the liquid-crystalline media comprise one or more compounds of the formula I and one or more compounds of the formula II.

The liquid-crystalline media in accordance with the present application preferably comprise in total 5 to 95%, preferably 10 to 90% and particularly preferably 15 to 80%, of compounds of the formula I.

The liquid-crystalline media in accordance with the present invention preferably comprise 10% or less, preferably 5% or less, particularly preferably 2% or less, very particularly preferably 1% or less, and in particular absolutely no compound having only two or fewer five- and/or six-membered rings.

The liquid-crystalline media in accordance with the present invention preferably comprise, more preferably predominantly consist of, even more preferably essentially consist of and very preferably completely consist of compounds selected from the group of the compounds of the formulae I and II.

In this application, "comprise" in connection with compositions means that the entity in question, i.e. the medium or the component, comprises the component or components or compound or compounds indicated, preferably in a total concentration of 10% or more and very preferably 20% or more.

In this connection, "predominantly consist of" means that the entity in question comprises 55% or more, preferably 60% or more and very preferably 70% or more, of the component or components or compound or compounds indicated.

In this connection, "essentially consist of" means that the entity in question comprises 80% or more, preferably 90% or more and very preferably 95% or more, of the component or components or compound or compounds indicated.

In this connection, "completely consist of" means that the entity in question comprises 98% or more, preferably 99% or more and very preferably 100.0%, of the component or components or compound or compounds indicated.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants and nanoparticles. The individual, added compounds are employed in concentrations of 0.01 to 6%, preferably 0.1 to 3%. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethylpiperidines or 2-benzotriazol-2-ylphenols. These assistants are known to the person skilled in the art and are commercially available, for example as light stabilisers.

An embodiment of the invention is therefore also a process for the preparation of a liquid-crystal medium which is characterised in that one or more compounds of the formula I are mixed with one or more further compounds and optionally with one or more additives. The further compounds are preferably selected from the compounds of the formula II, as indicated above, and optionally one or more further compounds In the present application, the expression dielectrically positive describes compounds or components where $\Delta\epsilon > 3.0$, dielectrically neutral describes those where $-1.5 \leq \Delta\epsilon \leq 3.0$ and dielectrically negative describes those where $\Delta\epsilon < -1.5$. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 µm. The voltage applied is a rectangular wave having a frequency of 1 kHz and an effective value of typically 0.5 V to 1.0 V, but it is always selected to be below the capacitive threshold of the respective test mixture.

$\Delta\epsilon$ is defined as $(\epsilon_\| - \epsilon_\perp)$, whereas $\epsilon_{average}$ is $(\epsilon_\| + 2\epsilon_\perp)/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties that are typical for liquid crystals are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\epsilon$) is determined at a frequency of 1 kHz. The threshold voltages, as well as all other electro-optical properties, are determined using test cells produced at Merck KGaA, Germany. The test cells for the determination of $\Delta\epsilon$ have a cell thickness of approximately 20 µm. The electrode is a circular ITO electrode having an area of 1.13 cm$^2$ and a guard ring. The orientation layers are SE-1211 from Nissan Chemicals, Japan, for homeotropic orientation ($\epsilon_\|$) and polyimide AL-1054 from Japan Synthetic Rubber, Japan, for homogeneous orientation ($\epsilon_\perp$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages are determined under perpendicular observation. The threshold ($V_{10}$), mid-grey ($V_{50}$) and saturation ($V_{90}$) voltages are determined for 10%, 50% and 90% relative contrast, respectively.

The liquid-crystalline media are investigated with respect to their properties in the microwave frequency range as described in A. Penirschke, S. Müller, P. Scheele, C. Weil, M. Wittek, C. Hock and R. Jakoby: "Cavity Perturbation Method for Characterization of Liquid Crystals up to 35

GHz", 34th European Microwave Conference—Amsterdam, pp. 545-548. Compare in this respect also A. Gaebler, F. Gölden, S. Müller, A. Penirschke and R. Jakoby "Direct Simulation of Material Permittivites . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced, for example, into a polytetrafluoroethylene (PTFE) or quartz capillary. The capillary has an internal radius of 180 μm and an external radius of 350 μm. The effective length is 2.0 cm. The filled capillary is introduced into the centre of the cavity with a resonance frequency of 30 GHz. This cavity has a length of 6.6 mm, a width of 7.1 mm and a height of 3.6 mm. The input signal (source) is then applied, and the result of the output signal is recorded using a commercial vector network analyser. For other frequencies (for example 19 Hz), the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in A. Penirschke, S. Müller, P. Scheele, C. Weil, M. Wittek, C. Hock and R. Jakoby: "Cavity Perturbation Method for Characterization of Liquid Crystals up to 35 GHz", 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

The dielectric anisotropy in the microwave range is defined as $$\Delta\epsilon_r = (\epsilon_{r,\parallel} - \epsilon_{r,\perp}).$$

The modulatability or tuneability (τ) is defined as $$\tau \equiv (\Delta\epsilon_r / \epsilon_{r,\parallel}).$$

The material quality (η) is defined as $$\eta \equiv (\tau / \tan \delta_{\epsilon^r,max}),$$

with the maximum dielectric loss factor $\tan \delta_{\epsilon^r,max}$:
$\tan \delta_{\epsilon^r,max} \equiv \max. \{\tan \delta_{\epsilon^r,\perp}; \tan \delta_{\epsilon^r,\parallel}\}$
which arises from the maximum value of the measured values for $\tan \delta_{\epsilon^r}$.

The material quality (η) of the preferred liquid-crystal materials is 5 or more, preferably 6 or more, preferably 8 or more, preferably 10 or more, preferably 15 or more, preferably 17 or more, particularly preferably 20 or more and very particularly preferably 25 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In the present application, the term compounds means both one compound and a plurality of compounds, unless expressly stated otherwise.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 180° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a cell thickness of 5 μm for at least 100 hours. At high temperatures, the clearing point is measured in capillaries by conventional methods.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The Δε of the liquid-crystal medium in accordance with the invention, at 1 kHz and 20° C., is preferably 1 or more, more preferably 2 or more and very preferably 3 or more.

The Δn of the liquid-crystal media in accordance with the present invention, at 589 nm (Na[D]) and 20° C., is preferably in the range from 0.20 or more to 0.90 or less, more preferably in the range from 0.25 or more to 0.90 or less, even more preferably in the range from 0.30 or more to 0.85 or less and very particularly preferably in the range from 0.35 or more to 0.80 or less.

In a preferred embodiment of the present application, the Δn of the liquid-crystal media in accordance with the present invention is preferably 0.50 or more, more preferably 0.55 or more.

Furthermore, the liquid-crystal media according to the invention are characterised by high anisotropies in the microwave range. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

In some embodiments, however, liquid crystals having a negative value of the dielectric anisotropy can also advantageously be used.

The liquid crystals employed are either individual substances or mixtures. They preferably have a nematic phase.

Preferred components which comprise a liquid-crystal medium or at least one compound in accordance with the invention are phase shifters, varactors, antenna arrays (for example for radio, mobile communications, microwave/radar and other data transmission), 'matching circuit adaptive filters' and others. Preference is given to components for high-frequency technology, as defined above. Preference is also given to components which can be modulated by different applied electrical voltages. Very particularly preferred components are phase shifters. In preferred embodiments, a plurality of phase shifters are functionally connected, giving, for example, a phase-controlled group antenna. A group antenna uses the phase shift of the transmitting or receiving elements arranged in a matrix in order to achieve bundling through interference. A parallel arrangement of phase shifters in row or grid form enables the construction of a so-called 'phased array', which can serve as tuneable transmitting or receiving antenna for high frequencies (for example gigahertz range). Phased array antennae according to the invention have a very broad usable reception cone.

Preferred applications are radar installations and data transmission equipment on manned or unmanned vehicles from the automobile, shipping, aircraft, space travel and satellite technology areas.

For the production of suitable components, in particular phase shifters, a liquid-crystalline medium according to the invention is typically introduced into rectangular cavities having a cross section of less than 1 mm and a length of several centimeters. The cavities have opposing electrodes mounted along two long sides. Such arrangements are familiar to the person skilled in the art. Through application of a variable voltage, the dielectric properties of the liquid-crystalline medium can be tuned in later operation in order to set different frequencies or directions of an antenna.

The term "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "alkoxy" preferably encompasses straight-chain radicals of the formula $C_nH_{2n+1}$—O—, in which n denotes 1 to 10. n is preferably 1 to 6. Preferred alkoxy groups are, for example, methoxy, ethoxy, n-propoxy, n-butoxy, n-pentoxy, n-hexoxy, n-heptoxy, n-octoxy, n-nonoxy, n-decoxy.

The term "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

The term "fluorinated alkyl radical" preferably encompasses mono- or polyfluorinated radicals. Perfluorinated radicals are included. Particular preference is given to $CF_3$, $CH_2CF_3$, $CH_2CHF_2$, $CHF_2$, $CH_2F$, $CHFCF_3$ and $CF_2CHFCF_3$.

The term "fluorinated alkoxy radical" encompasses mono- or polyfluorinated radicals. Perfluorinated radicals are preferred. Particular preference is given to the $OCF_3$ radical.

In the present application, high-frequency technology means applications having frequencies in the range from 1 MHz to 1 THz, preferably from 1 GHz to 500 GHz, more preferably 2 GHz to 300 GHz, particularly preferably from 5 to 150 GHz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

The liquid-crystal media according to the invention consist of a plurality of compounds, preferably 3 to 30, more preferably 4 to 20 and very preferably 4 to 16, compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present application, high-frequency technology means applications having frequencies in the range from 1 MHz to 1 THz, preferably from 1 GHz to 500 GHz, preferably 2 GHz to 300 GHz, particularly preferably from about 5 to 150 GHz. The application is preferably in the microwave spectrum or adjacent regions suitable for communications transfer in which 'phased array' modules can be used in transmitting and receiving antennae.

In the present application and in the following examples, the structures of the liquid-crystal compounds are indicated by means of acronyms, where the transformation into chemical formulae is carried out in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |

-continued
| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nOF | $OC_nH_{2n+1}$ | F | H | H |
| nF.F | $C_nH_{2n+1}$ | F | F | H |
| nF.F.F | $C_nH_{2n+1}$ | F | F | F |
| nOCF$_3$ | $C_nH_{2n+1}$ | $OCF_3$ | H | H |
| nOCF$_3$.F | $C_nH_{2n+1}$ | $OCF_3$ | F | H |
| n-Vm | $C_nH_{2n+1}$ | $-CH=CH-C_mH_{2m+1}$ | H | H |
| nV-Vm | $C_nH_{2n+1}-CH=CH-$ | $-CH=CH-C_mH_{2m+1}$ | H | H |
Suitable mixture components are given in Tables A and B.
TABLE A
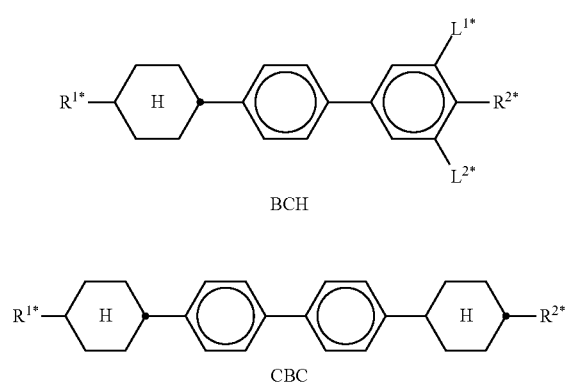
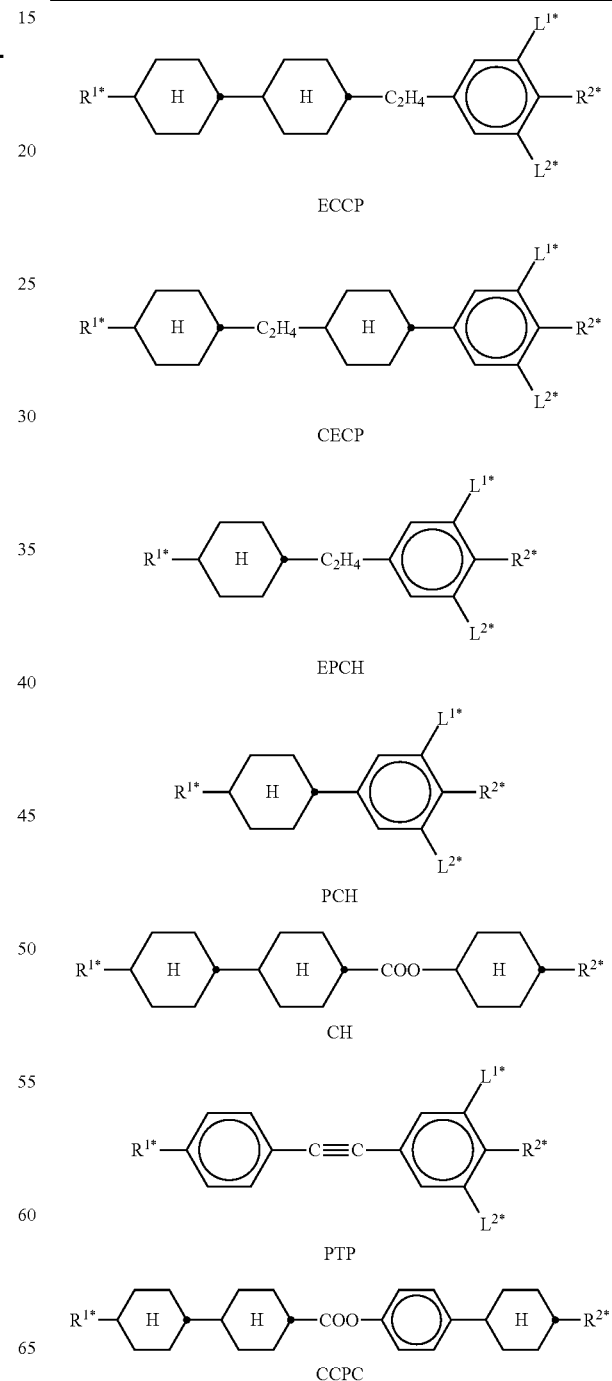

TABLE A-continued

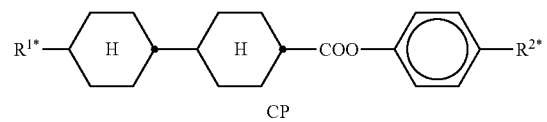

CP

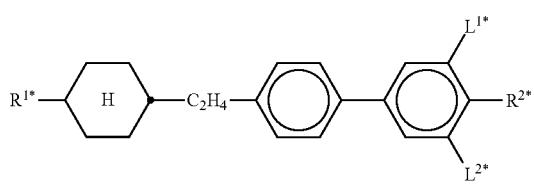

BECH

TABLE B

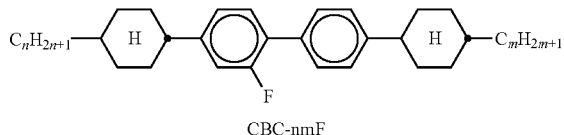

CBC-nmF

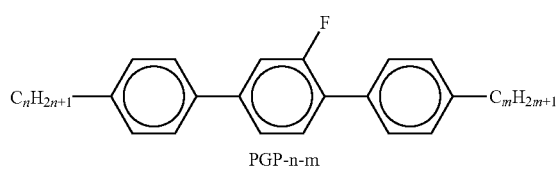

PGP-n-m

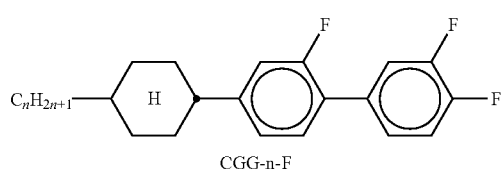

CGG-n-F

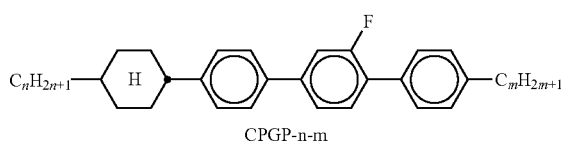

CPGP-n-m

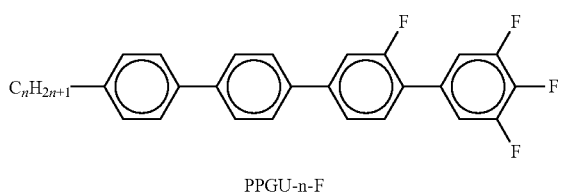

PPGU-n-F

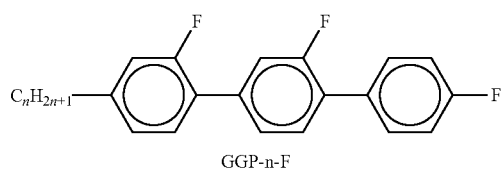

GGP-n-F

TABLE B-continued

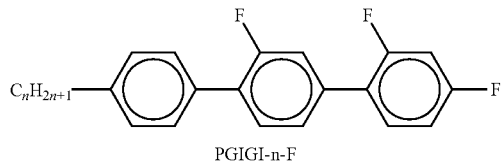

PGIGI-n-F

The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

EXAMPLES

The acetylenes and boronic acids employed are commercially available, the 1,1,2-trifluorotriethylsilylethene building block is synthesised by standard laboratory procedures.

Synthesis Example 1: 1-Iodo-4-bromonaphthalene

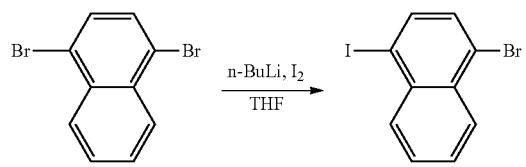

100 g (350 mmol) of 1,4-dibromonaphthalene are initially introduced in 1 l of THF, cooled to −70° C., and 235 ml of n-BuLi (1.6 M in hexane, 370 mmol) are added dropwise. After 1 h, 103 g of $I_2$ (406 mmol) in 250 ml of THF are added dropwise, the mixture is stirred at −70° C. for a further 2 h, warmed to 0° C. and quenched by the addition of 50 ml (644 mmol) of aqueous $NaHSO_3$ solution (w=39%).

The phases are separated, and the aqueous phase is extracted once with MTB. The combined organic phases are washed with saturated sodium chloride solution, dried over sodium sulfate, filtered and evaporated in a rotary evaporator. The residue is purified by column chromatography ($SiO_2$, heptane), and the further purification is carried out by recrystallisation from isopropanol, giving 1-iodo-4-bromonaphthalene as a yellow solid.

Synthesis Example 2:
1-Bromo-4-(4-n-propylphenylethynyl)naphthalene

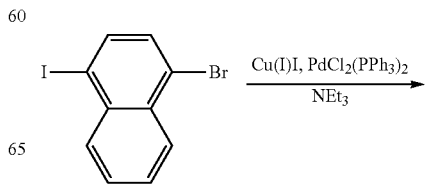

-continued

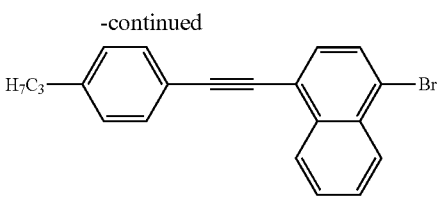

15.3 g (43.6 mmol) of 1-iodo-4-bromonaphthalene and 7.25 g (5.3 mmol) of 4-n-propylphenylacetylene are initially introduced in 200 ml of NEt$_3$, 170 mg (0.9 mmol) of copper(I) iodide and 600 mg (0.9 mmol) of bis-(triphenylphosphine)palladium(II) chloride are added, and the mixture is refluxed for 30 minutes. The batch is cooled, water and heptane are added, and the phases are separated. The organic phase is washed with saturated sodium chloride solution, dried over sodium sulfate, filtered and evaporated in a rotary evaporator. The residue is purified by column chromatography (SiO$_2$, heptane), and the further purification is carried out by recrystallisation from isopropanol.

Synthesis Example 3: 1-(4-n-Propylphenylethynyl)-4-(Z-1,2-difluoro-2-triethylsilylethylenyl)naphthalene

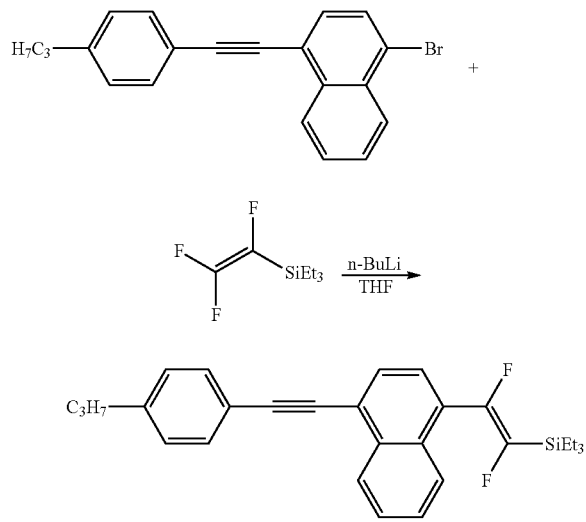

4.9 g (13.2 mmol) of 1-bromo-4-(4-n-propylphenylethynyl)naphthalene are initially introduced in 100 ml of THF and cooled to −70° C., and 9 ml of n-BuLi (1.6 M in hexane, 14.3 mmol) are added dropwise. After 1 h, 4 g (19.6 mmol) of pure 1,1,2-trifluorotriethylsilylethene are added, and the batch is warmed overnight at RT, before being quenched by the addition of semisaturated ammonium chloride solution. The batch is diluted with MTB, and the phases are separated. The aqueous phase is extracted with MTB, the combined organic phases are washed with saturated sodium chloride solution, dried over sodium sulfate, filtered and evaporated in a rotary evaporator. The residue is purified by column chromatography (SiO$_2$, heptane→heptane/MTB=10:1).

Synthesis Example 4: 1-(4-n-Propylphenylethynyl)-4-(E-1,2-difluoroethylenyl)naphthalene

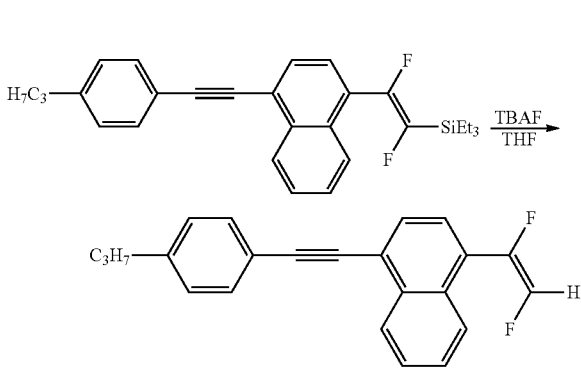

The product obtained from the previous step (13.2 mmol) is initially introduced in 100 ml of THF and 5 ml of water, and 13 ml of a solution of tetrabutylammonium fluoride (1 M in THF, 13 mmol) are added. The batch is stirred overnight at RT and quenched by the addition of semisaturated sodium chloride solution and MTB. The phases are separated, and the organic phase is dried over sodium sulfate, filtered and evaporated in a rotary evaporator. The residue is purified by column chromatography (SiO$_2$, heptane).

Synthesis Example 5: 1-(4-n-Propylphenylethynyl)-4-(Z-1,2-difluoro-2-iodo-ethylenyl)naphthalene

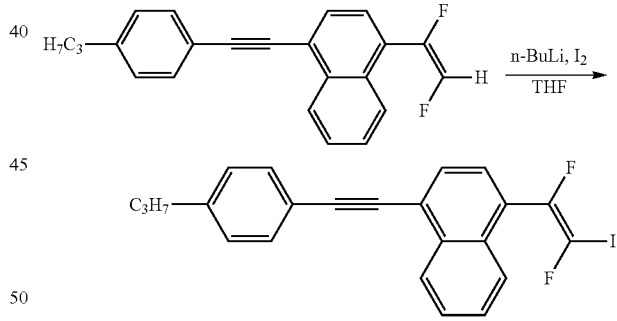

The product obtained from the previous step (6 mmol) is initially introduced in 55 ml of THF and cooled to −70° C., and 4.3 ml of n-BuLi (1.6 M in hexane, 6.8 mmol) are added dropwise. After 1 h, 1.9 g (7.5 mmol) of iodine in 15 ml of THF are added, and the mixture is stirred at −60° C. for 1 h. The batch is subsequently warmed to 0° C. and quenched by the addition of water. 1 g (4 mmol) of sodium thiosulfate pentahydrate and MTB are then added, and the phases are separated. The aqueous phase is extracted with MTB, and the combined organic phases are washed with saturated sodium chloride solution, dried over sodium sulfate, filtered and evaporated in a rotary evaporator. The residue is purified by column chromatography (SiO$_2$, heptane).

Synthesis Example 6: 1-(4-n-Propylphenylethynyl)-4-[E-1,2-difluoro-2-(4-trifluoromethylphenyl)ethylenyl]naphthalene

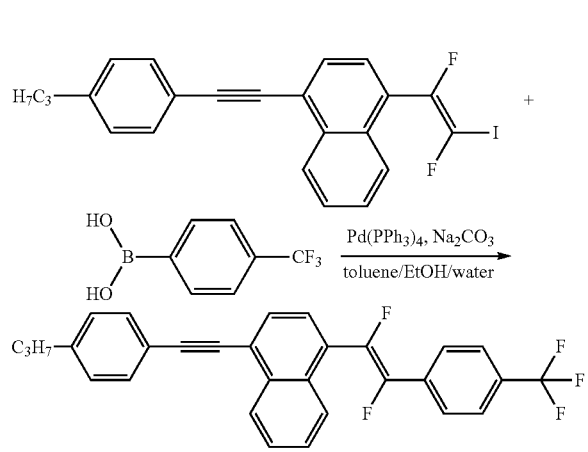

2.48 mmol of iodide and 3.16 mmol of boronic acid are initially introduced in 30 ml of toluene, and 0.6 g (2.28 mmol) of $Na_2CO_3$ in 15 ml of water and 4 ml of EtOH are added, before 150 mg (0.13 mmol) of tetrakis(triphenylphosphine)palladium(0) are added. The batch is refluxed for 16 h and cooled, and the phases are separated. The aqueous phase is extracted with toluene, and the combined organic phases are washed with saturated sodium chloride solution, dried over sodium sulfate, filtered and evaporated in a rotary evaporator. The residue is purified by column chromatography ($SiO_2$, heptane), and the further purification is carried out by recrystallisation from heptane/EtOH=20:1.

MS (EI): m/e (%)=476 (100, M$^+$), 447 (58, [M–ethyl]$^+$)
Δ∈=+10.9
Δn=0.33
$\gamma_1$=3238 mPa·s
C 125 N 167 I The following are prepared analogously to Synthesis Examples 1 to 6:

Synthesis Example 7: 1-(4-n-Propylphenylethynyl)-4-[E-1,2-difluoro-2-(4-n-butylphenyl)ethylenyl]naphthalene

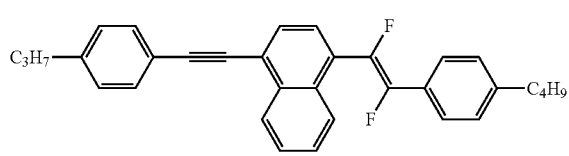

The title compound is prepared analogously to Example 6 using 4-n-butyl-phenylboronic acid.

MS (EI): m/e (%)=464 (100, M$^+$), 435 (10, [M–ethyl]$^+$), 421 (7, [M–propyl]$^+$), 392 (3, [M–propyl-ethyl]$^+$), 196 (11, [M–propylethyl]$^{2+}$).
Δ∈=+1.6
Δn=0.34
$\gamma_1$=2244 mPa·s
Tg –34 C 67 N 181 I

Synthesis Example 8: 1-(4-n-Propylphenylethynyl)-4-[E-1,2-difluoro-2-(3,4,5-trifluorophenyl)ethylenyl]naphthalene

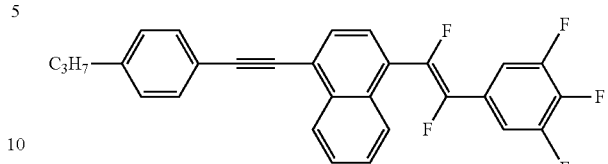

Synthesis Example 9: 1-(4-n-Butylphenylethynyl)-4-[E-1,2-difluoro-2-(3,4,5-trifluorophenyl)ethylenyl]naphthalene

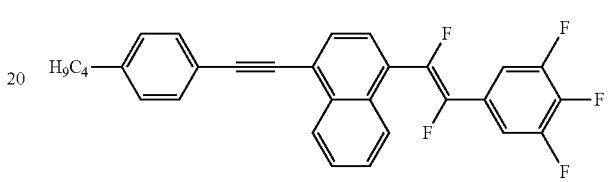

MS (EI): m/e (%)=476 (100, M$^+$), 433 (65, [M–propyl]$^+$).
Δ∈=+12.3
Δn=0.31
$\gamma_1$=1627 mPa·s
C 111 N (87) I

Synthesis Example 10: 1-(4-n-Butylphenylethynyl)-4-[E-1,2-difluoro-2-(4-n-butylphenyl)ethylenyl]naphthalene (1)

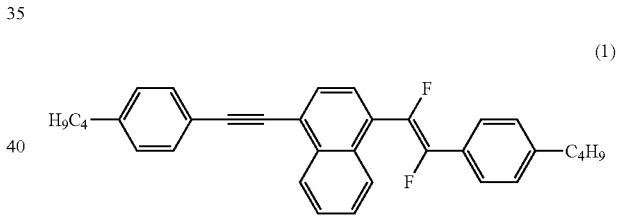

MS (EI): m/e (%)=478 (100, M$^+$), 435 (27, [M–propyl]$^+$).
Δ∈=+0.8
Δn=0.31
$\gamma_1$=2018 mPa·s
Tg –37 C 65 N 162 I

Synthesis Example 11: 1-(4-n-Butylphenylethynyl)-4-[E-1,2-difluoro-2-(2,3-difluoro-3-ethoxyphenyl)ethylenyl]naphthalene

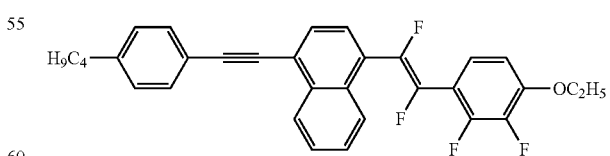

MS (EI): m/e (%)=502 (100, M$^+$), 459 (22, [M–propyl]$^+$), 431 (18, [M–propylethyl]$^+$).
Δ∈=–3.6
Δn=0.30
$\gamma_1$=3920 mPa·s
Tg –10 C 98 N 195 I Synthesis Example 12: 1,4-Bis-[E-1,2-difluoro-2-(4-n-butylphenyl)-ethylenyl]naphthalene

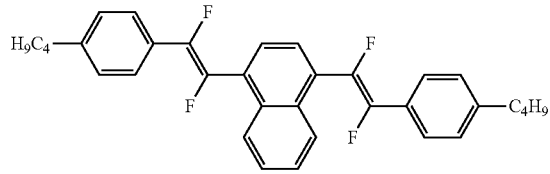

MS (EI): m/e (%)=516 (100, M⁺).
Δε=+1.3
Δn=0.23
γ₁=2855 mPa·s
C 88 N 141 I

Synthesis Example 13: 4-(2-{(4-[1,2-Difluoro-2-(4-methylnaphthalen-1-yl)-vinyl]naphthalen-1-yl}-1,2-difluorovinyl)-2'-fluoro-4''-pentyl[1,1';4',1'']terphenyl

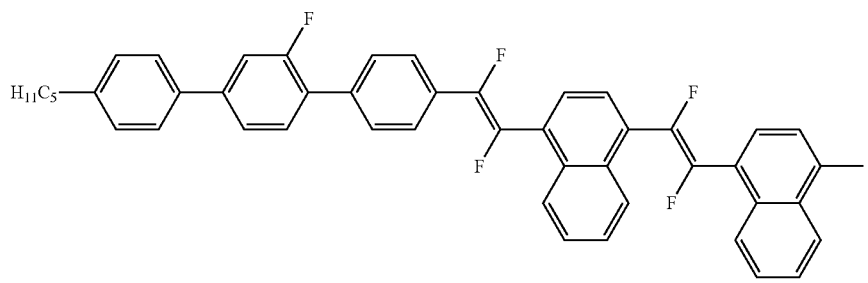

MS (EI): m/e (%)=708 (100, M⁺), 325.5 (12, [M−butyl]²⁺).
C 205 N 312 I

Synthesis Example 14

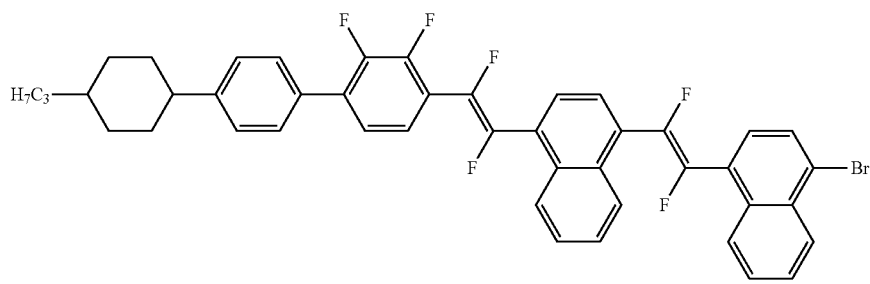

MS (EI): m/e (%)=768 (100, M⁺), 690 (10, [M−Br]⁺).
Δε=+2.4
Δn=0.41
γ₁=63815 mPa·s
C 176 N 318 I

Mixture Example 1

A liquid-crystal mixture M-1 having the composition and properties as indicated in the following table is prepared. Compound (I) originates from Synthesis Example 10.

| Composition | | |
|---|---|---|
| Compound No. | Abbreviation | |
| 1 | BCH-3F.F | 10.8% |
| 2 | BCH-5F.F | 9.00% |
| 3 | ECCP-30CF3 | 4.50% |
| 4 | ECCP-50CF3 | 4.50% |
| 5 | CBC-33F | 1.80% |
| 6 | CBC-53F | 1.80% |
| 7 | CBC-55F | 1.80% |
| 8 | PCH-6F | 7.20% |
| 9 | PCH-7F | 5.40% |
| 10 | CCP-20CF3 | 7.20% |
| 11 | CCP-30CF3 | 10.8% |
| 12 | CCP-40CF3 | 6.30% |
| 13 | CCP-50CF3 | 9.90% |
| 14 | PCH-5F | 9.00% |
| 15 | (1) | 10.0% |
| Σ | | 100.0% |

-continued

| Physical properties | |
|---|---|
| T(N, I) = | 99° C. |
| Δn (20° C., 589.3 nm) = | 0.120 |

-continued

| | |
|---|---|
| Δε (20° C., 1 kHz) = | 4.9 |
| γ₁ (20° C.) = | 179 mPa·s |

This mixture is used for applications in the microwave area, in particular for phase shifters ('phased arrays').

For comparison, a mixture C-1 without component (1) is prepared from compound Nos. 1-14 of M-1, where compound Nos. 1-14 are present in the same relative amounts.

TABLE 5

| Properties of mixture M-1 and C-2 at 19 GHz (20° C.) | | | | | |
|---|---|---|---|---|---|
| Mixture | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
| M-1 | 2.58 | 2.33 | 0.097 | 0.0041 | 0.0125 | 7.79 |
| C-1 | 2.49 | 2.30 | 0.079 | 0.0048 | 0.0139 | 5.70 |

The tunability $\tau$ and the material quality $\eta$ are improved compared with comparative mixture C-1.

Further combinations of the embodiments and variants of the invention in accordance with the description also arise from the following claims.

The invention claimed is:

1. Compounds of the formula I

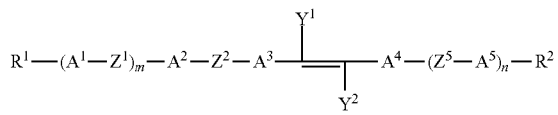

I in which $A^{1-5}$, independently of one another, denote a) a radical of the formula

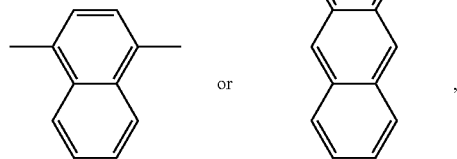

b) 1,4-phenylene, in which one or more CH groups may be replaced by N, c) trans-1,4-cyclohexylene or cyclohexenylene, in which, in addition, one or two non-adjacent CH$_2$ groups may be replaced by —O— and/or —S— and in which H may be replaced by F, or d) a radical from the group 1,4-bicyclo[2.2.2]octylene, cyclobut-1,3-diyl, spiro[3.3]heptane-2,6-diyl,

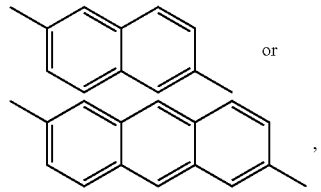

and in which, in groups a), b), c) and d), one or more H atoms may also be replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group, and where at least one radical from A$^1$ to A$^5$ represents a radical according to a), R$^1$ and R$^2$ each, independently of one another, denote a halogenated or unsubstituted alkyl radical having 2 to 10 C atoms, where, in addition, one or more CH$_2$ groups in these radicals may each be replaced, independently of one another, by —C≡C—, —CH=CH—, —CF=CF—, —CF=CH—, —CH=CF—, —(CO)O—, —O(CO)—, —(CO)— or —S— in such a way that O or S atoms are not linked directly to one another, or F, Br, CN, CF$_3$, OCF$_3$, SCN, NCS or SF$_5$, Z$^2$ denotes —C≡C— or

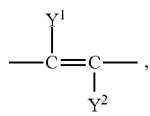

Y$^1$, Y$^2$, denote F,

Z$^1$, Z$^5$, independently of one another, denote a single bond, —C≡C—, —CH=CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH=CF— or —CF=CF—, where asymmetrical bridges may be oriented to both sides, and m, n, independently of one another, denote 0, 1 or 2.

2. Compounds according to claim 1, characterised in that at least one group from A$^2$, A$^3$ and A$^4$ denotes an optionally substituted 1,4-naphthylene radical or a 1,4-anthracenylene radical.

3. Compounds according to claim 1, characterised in that the compounds of the formula I contain one or two optionally substituted 1,4-naphthylene radicals or 1,4-anthracenylene radicals.

4. Compounds according to claim 1, characterised in that m and n are 0.

5. Liquid-crystal medium, characterised in that it comprises one or more compounds of the formula I

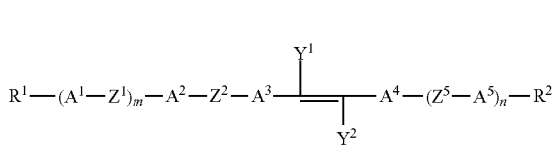

I in which

A$^{1-5}$, independently of one another, denote a) a radical of the formula

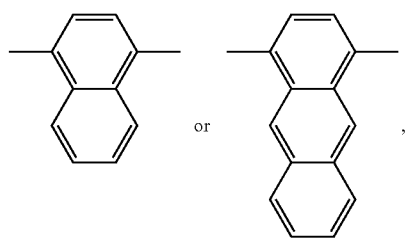

b) 1,4-phenylene, in which one or more CH groups may be replaced by N, c) trans-1,4-cyclohexylene or cyclohexenylene, in which, in addition, one or two non-adjacent CH$_2$ groups may be replaced by —O— and/or —S— and in which H may be replaced by F, or d) a radical from the group 1,4-bicyclo[2.2.2]octylene, cyclobut-1,3-diyl, spiro[3.3]heptane-2,6-diyl,

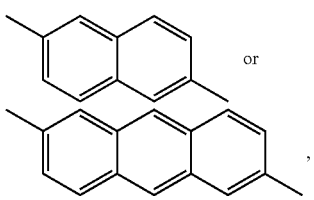 or and in which, in groups a), b), c) and d),
one or more H atoms may also be replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group,
and where
at least one radical from A$^1$ to A$^5$ represents a radical according to a),
R$^1$ and R$^2$ each, independently of one another, denote a halogenated or unsubstituted alkyl radical having 2 to 10 C atoms, where, in addition, one or more CH$_2$ groups in these radicals may each be replaced, independently of one another, by —C≡C—, —CH=CH—, —CF=CF—, —CF=CH—, —CH=CF—, —(CO)O—, —O(CO)—, —(CO)— or —S— in such a way that O or S atoms are not linked directly to one another,
or F, Br, CN, CF$_3$, OCF$_3$, SCN, NCS or SF$_5$,
Z$^2$ denotes C≡C— or

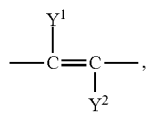

Y$^1$, Y$^2$, independently of one another, denote H, F, Cl, or C$_1$-C$_{10}$ alkyl,
Z$^1$, Z$^5$, independently of one another, denote a single bond, —C≡C—, —CH=CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH=CF— or —CF=CF—, where asymmetrical bridges may be oriented to both sides, and
m, n, independently of one another, denote 0, 1 or 2.

6. Liquid-crystal medium according to claim 5, characterised in that it additionally comprises one or more compounds selected from the compounds of the formula II:

II

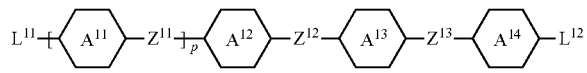

in which
L$^{11}$ denotes R$^{11}$ or X$^{11}$,
L$^{12}$ denotes R$^{12}$ or X$^{12}$,
R$^{11}$ and R$^{12}$, independently of one another, denote unfluorinated alkyl or unfluorinated alkoxy having 1 to 17 C atoms or unfluorinated alkenyl, unfluorinated alkenyloxy, or unfluorinated alkoxyalkyl having 2 to 15 C atoms,
X$^{11}$ and X$^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms,
p denotes 0 or 1,
Z$^{11}$ to Z$^{13}$, independently of one another, denote trans-CH=CH—, trans-CF=CF—, —C≡C— or a single bond, and

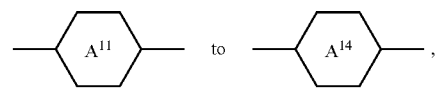

independently of one another, denote
a) 1,4-phenylene, in which one or more, preferably one or two, CH groups may be replaced by N,
b) trans-1,4-cyclohexylene or cyclohexenylene, in which, in addition, one or two non-adjacent CH$_2$ groups may be replaced by —O— and/or —S— and in which H may be replaced by F,
and in which, in groups a) and b), one or more H atoms may also be replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group.

7. Liquid-crystal medium according to claim 5, characterised in that the concentration of the compounds of the formula I in the medium is in the range from in total 5% to 95%.

8. A method comprising adding a compound of the formula I according to claim 5 to a liquid-crystalline mixture.

9. A method comprising adding a compound of the formula I according to claim 1 to a component for high-frequency technology.

10. Process for the preparation of a liquid-crystal medium according to claim 5, characterised in that one or more compounds of the formula I are mixed with one or more further compounds and optionally with one or more additives.

11. Component for high-frequency technology, characterised in that it comprises a liquid-crystal medium according to claim 5.

12. Component according to claim 11, characterised in that it is one or more functionally connected phase shifters.

13. A method comprising incorporating a liquid-crystal medium according to claim 5 in a component for high-frequency technology.

14. Phase-controlled group antenna, characterised in that it comprises one or more components according to claim 11.

15. Liquid-crystal medium according to claim 5, wherein for one or more compounds of the formula I, Y$^1$ and Y$^2$ denote F.

* * * * *